US012751706B2

(12) United States Patent
Abrol

(10) Patent No.: US 12,751,706 B2
(45) Date of Patent: Oct. 6, 2026

(54) MEDICAL SYSTEMS, DEVICES, AND RELATED METHODS FOR TRACTION IN TISSUE REMOVAL

(71) Applicant: BOSTON SCIENTIFIC MEDICAL DEVICE LIMITED, Galway (IE)

(72) Inventor: Sanchita Abrol, New Delhi (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 77 days.

(21) Appl. No.: 18/922,501

(22) Filed: Oct. 22, 2024

(65) Prior Publication Data

US 2025/0134511 A1 May 1, 2025

Related U.S. Application Data

(60) Provisional application No. 63/593,268, filed on Oct. 26, 2023.

(51) Int. Cl.
*A61B 17/02* (2006.01)
*A61B 17/00* (2006.01)
*A61B 17/064* (2006.01)

(52) U.S. Cl.
CPC ................................ *A61B 17/0218* (2013.01); *A61B 2017/00269* (2013.01); *A61B 2017/00477* (2013.01); *A61B 2017/00862* (2013.01); *A61B 2017/0647* (2013.01)

(58) Field of Classification Search
CPC ...... A61B 17/0218; A61B 2017/00269; A61B 2017/0034; A61B 2017/0225; A61B 2017/00477; A61B 17/083; A61B 1/0014; A61B 17/10; A61B 17/320016; A61B 17/00234; A61B 2017/00349; A61B 2017/00862; A61B 17/0281; A61B 2017/0647
See application file for complete search history.

(56) References Cited

U.S. PATENT DOCUMENTS

| | | | |
|---|---|---|---|
| 5,379,759 | A | 1/1995 | Sewell, Jr. |
| 10,905,467 | B2 | 2/2021 | Goto |
| 2012/0316593 | A1 | 12/2012 | Kim |
| 2015/0351855 | A1 | 12/2015 | Lee et al. |
| 2017/0189006 | A1 | 7/2017 | Shluzas et al. |
| 2020/0360006 | A1 | 11/2020 | Sluti et al. |
| 2021/0205006 | A1 | 7/2021 | Sharma |
| 2022/0338855 | A1 | 10/2022 | Smith et al. |

FOREIGN PATENT DOCUMENTS

| | | | |
|---|---|---|---|
| JP | 2005103107 | * | 4/2005 |
| JP | 2005103107 | A | 4/2005 |
| KR | 20210124571 | A | 10/2021 |

* cited by examiner

*Primary Examiner* — Katherine M Shi
(74) *Attorney, Agent, or Firm* — Bookoff McAndrews PLLC

(57) ABSTRACT

A medical device includes a connection member for connecting a homeostasis clip to the medical device; a biasing member, wherein the biasing member biases the medical device toward a compressed configuration; and a needle with at least one barb. The connection member is connected to the biasing member such that, with the needle inserted into tissue past the at least one barb and the biasing member pulled toward a tensioned configuration by the homeostasis clip connected to the connection member, the needle and the at least one barb pull the tissue in a direction parallel to a direction of tension placed on the biasing member.

11 Claims, 8 Drawing Sheets

MEDICAL SYSTEMS, DEVICES, AND RELATED METHODS FOR TRACTION IN TISSUE REMOVAL

CROSS-REFERENCE TO RELATED APPLICATIONS

This application claims the benefit of priority to U.S. Provisional Application No. 63/593,268, filed on Oct. 26, 2023, which is incorporated by reference herein in its entirety.

TECHNICAL FIELD

Aspects of this disclosure generally relate to medical systems, devices, and related methods. In particular, aspects of this disclosure relate to medical systems, devices, and related methods for traction in tissue removal.

BACKGROUND

Endoscopic submucosal dissection (ESD) is a technique for the minimally invasive removal of tumors and lesions, especially gastrointestinal tumors and lesions. This procedure offers several advantages, including reduced patient discomfort, shorter hospital stays, and/or faster recovery times when compared to many other surgical methods. However, ESD procedures often rely heavily on precise and/or controlled tissue manipulation, which may be challenging due to the anatomical complexities of the gastrointestinal tract. To address these challenges, traction devices are often used to facilitate visualization and/or manipulation of the mucosal and submucosal layers during ESD procedures.

While traction devices improve the feasibility and safety of ESD, current devices have certain limitations. For example, many traction devices and related methods employ grasping forceps or clips, which may cause tissue trauma, hinder the endoscope's movement, or obscure a user's view. Moreover, these devices often require complex setup or assembly, specialized training, or multiple personnel for effective utilization, which may increase the costs, risks, duration, etc. of the procedure.

Systems, devices, and methods of the current disclosure may rectify some of the deficiencies described above or address other aspects of the art.

SUMMARY

Examples of this disclosure relate to, among other things, medical devices configured for increasing traction during tissue removal.

In one aspect, a medical device may include a connection member for connecting a homeostasis clip to the medical device; a biasing member; and a needle with at least one barb. The biasing member may bias the medical device toward a compressed configuration. The connection member may be connected to the biasing member such that, with the needle inserted into tissue past the at least one barb and the biasing member pulled toward a tensioned configuration by the homeostasis clip connected to the connection member, the needle and the at least one barb may pull the tissue in a direction parallel to a direction of tension placed on the biasing member.

In some aspects, the medical device may include a longitudinal axis, and the biasing member may apply tension along the longitudinal axis when pulled by the connection member. The medical device may further include a base member, and the base member may be coupled to the connection member and the biasing member. The base member may include a disc having two holes for connecting the connection member to the disc. The base member may be a flat circular plate that may have one or more connection portions for connecting to the connection member. The medical device may also have a needle base member that couples the biasing member and the needle. The needle may include a plurality of barbs on at least two sides of the needle. At least one of the barbs may include one or more projections that extend at an angle that is not parallel to a longitudinal axis of the needle. The connection member may include a loop made from one or more of nylon and linear low density polyethylene. The connection member may be configured to be removably coupled to a subject's anatomy with a homeostasis clip. The biasing member may comprise stainless steel. The needle may have four projections at a distal end of the needle. The projections at the distal end of the needle may be of equivalent size. The connection member may be capable of being cut by an end effector of one or more medical device systems to sever the connection member. The connection member may be formed from one or more of nylon and linear low density polyethylene.

In another aspect, a tissue traction device may include: a biasing member comprising a compliant or semi-compliant material biasing the tissue traction device toward a compressed configuration; a needle attached to a distal end of the biasing member; and a connection member attached to proximal end of the biasing member. The needle may include one or more projections at a distal end of the needle that are angled away from a longitudinal axis of the needle so as to impede removal of the needle from tissue, and the connection member may include a first end and a second end and the first end and the second end of the second attachment member are coupled to the biasing member. The tissue traction device may also include a needle base member that couples the biasing member and the needle.

In yet another aspect, a method of resecting tissue from a body lumen of a subject includes: inserting a needle including at least one barb into a tissue of a subject, the needle being positioned at a distal portion of a medical device comprising the needle, a connection member, and a biasing member coupling the needle with the connection member; coupling the connection member to a portion of a subject's anatomy to anchor the medical device; commencing a resection of the tissue, wherein the tension on the biasing member eases as the tissue is resected; and fully resecting the tissue from surrounding tissue. The biasing member can include a compliant or semi-compliant material biasing the biasing member toward a compressed configuration. The connection member may be clipped to a portion of the subject's anatomy with a homeostasis clip to place the biasing member under tension.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Examples of this disclosure include medical systems, devices, and related methods for traction in tissue removal. The systems, devices, and methods discussed herein may help to overcome the shortcomings of existing systems, devices, and methods, for example, helping to provide users (e.g., surgeons) with a more effective and/or user-friendly system or tool for endoscopic submucosal dissection (ESD). It is to be noted, however, that the scope of subject matter of this application is defined by the features listed in the claims, and not an ability to rectify any particular deficiency.

Reference will now be made in detail to examples of this disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body of a subject or closer to a user, such as a medical professional, holding or otherwise using a medical device (e.g., an endoscope) to insert the traction devices described herein into tissue. In contrast, "distal" refers to a position relatively further away from the medical professional or other user holding or otherwise using the medical device, or closer to the interior of the subject's body. As used herein, the terms "comprises," "comprising," "has," "having," "includes," "including," or other variations thereof, are intended to cover a non-exclusive inclusion, such that a system(s), device(s), or method(s) that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figure 1:
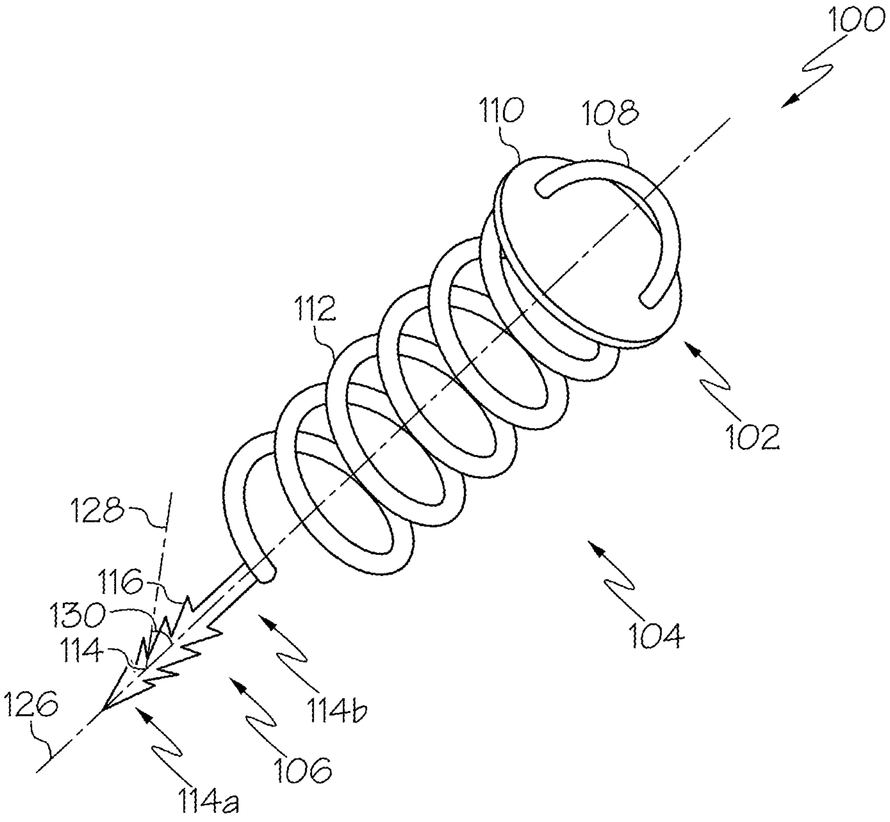
FIG. 1 illustrates a medical device for increased traction during tissue removal according to one or more embodiments shown and described herein.
Figure 2A:
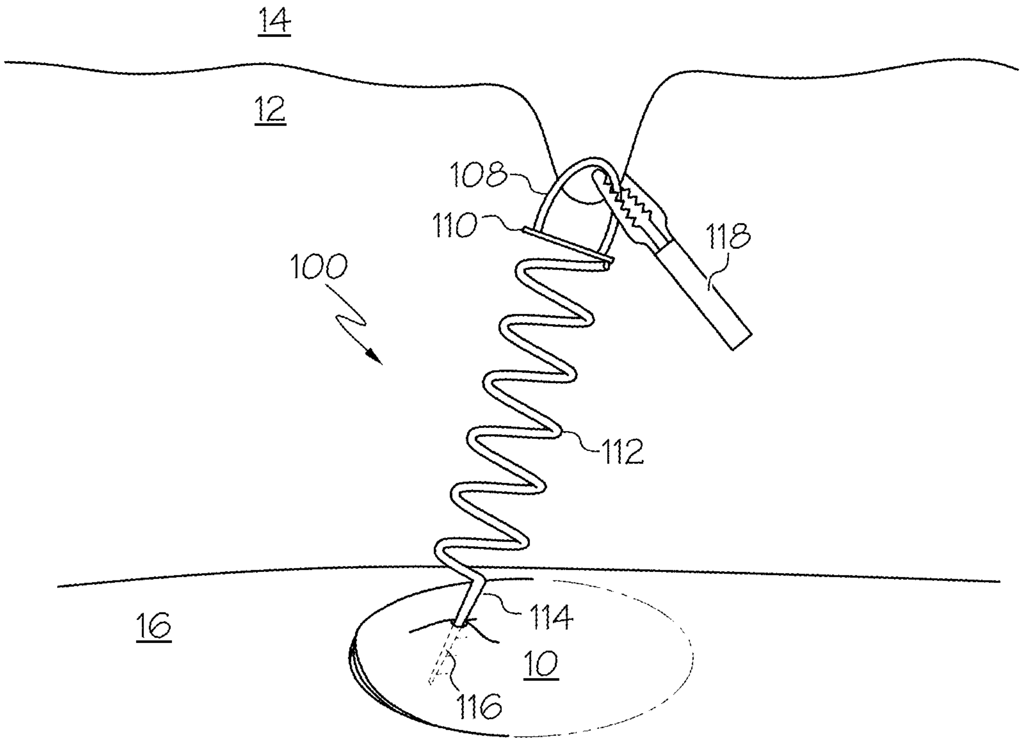
FIGS. 2A-2C illustrate stages of removing tissue using a medical system that includes the medical device of FIG. 1.
Figure 2B:
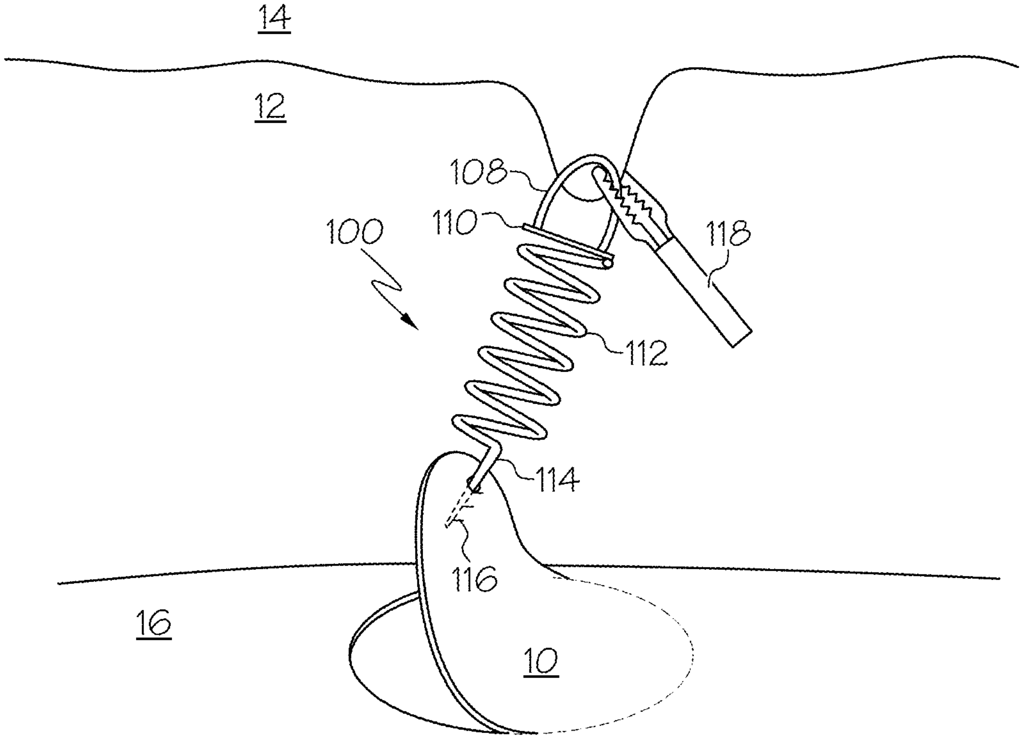
Figure 2C:
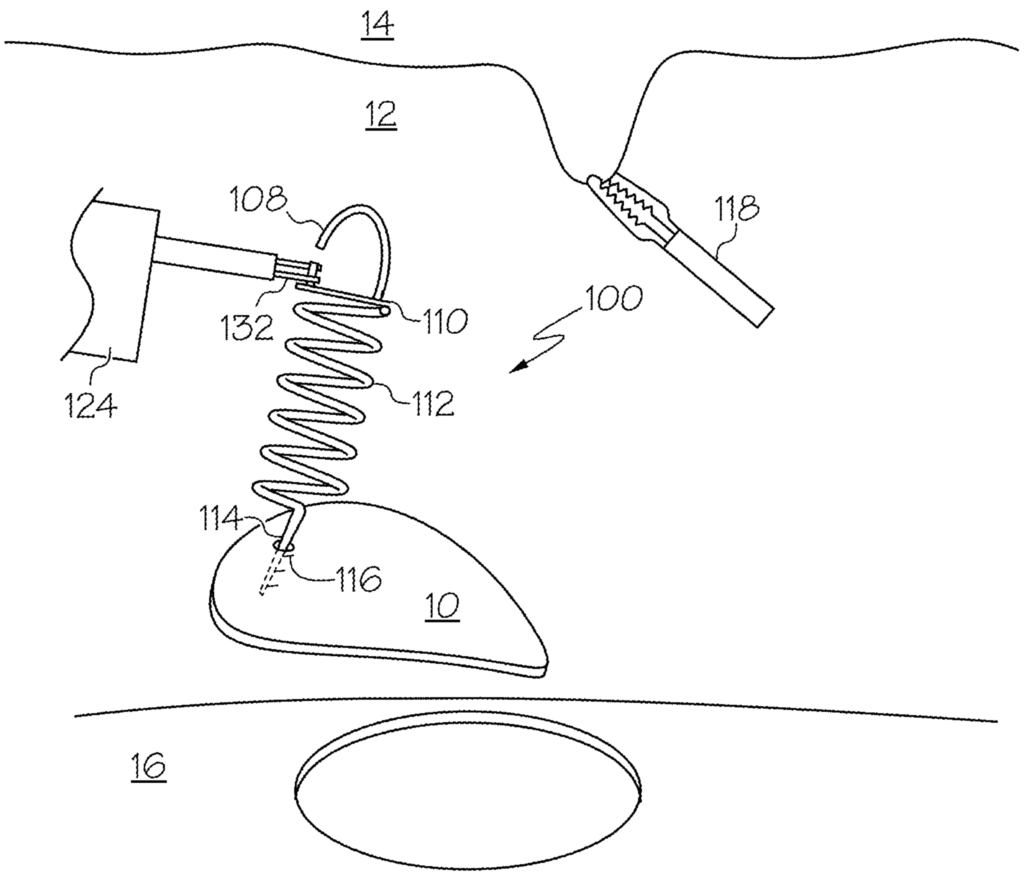

FIG. 1 shows a medical device 100 that can be used to help increase traction within a subject. The medical device 100 includes a proximal portion 102, an intermediate or medial portion 104, and a distal portion 106. The proximal portion 102 includes a connection member 108 for connecting the medical device 100 to another device (e.g., a clip 118 (e.g., a homeostasis clip as shown in FIGS. 2A-2C) or other clip). The connection between the connection member 108 and the other device may be direct, as discussed below. The medial portion 104 can include a base member 110 and a biasing member 112. The distal portion 106 includes a needle 114, which may include at least one barb 116.

The biasing member 112 can be made from a compliant or semi-compliant material and may bias the medical device 100 toward a compressed configuration and/or an expanded configuration depending on a tuning of the biasing member as described in greater detail herein. In some embodiments, the connection member 108 is connected to the base member 110. In these aspects, with the needle 114 inserted into tissue (e.g., such that the barb 116 is positioned within the tissue) at a target site (e.g., tissue of the subject inside the subjects GI tract), the biasing member 112 can be pulled or urged toward the expanded configuration by the clip 118 connected to the connection member 108. In these aspects, the biasing member 112 may help to place tension on the tissue at the target site, for example, at least partially in a direction parallel to the direction of tension of the biasing member 112.

The features of the medical device 100 may generally extend from the proximal portion 102 to the distal portion 106 along a longitudinal axis 126 of the medical device 100. The longitudinal axis 126 may be common to one or more features of the medical device 100. The barbs 116 may be projections that extend away from the longitudinal axis 126 at an angle 130 along a barb axis 128. In these aspects, with the needle 114 at least partially inserted into tissue, the barbs 116 may help to impede removal of the needle 114 from the tissue when the medical device 100 is pulled or urged away from the tissue. That is, in some aspects, the barbs 116 may be non-parallel with the longitudinal axis 126 of the medical device 100.

The connection member 108 can be a semi-rigid, or pliable structure that forms a loop or partial loop that provides a structure for connecting one or more external devices or features to the medical device 100. The connection member 108 can be made from one or more materials including, for example, nylon, linear low density polyethylene (LLDPE), low density polyethylene (LDPE), medium density polyethylene (MDPE), polytetrafluoroethylene (PTFE), polychlorotrifluoroethylene (PCTFE), perfluoroalkoxy (PFA), tetrafluorethylene-perfluoropropylene (FEP), or one or more other materials.

The base member 110 may be a disc-shaped (i.e., flat and circular) portion of the medical device 100 that may include one or more features for connecting the connection member 108 with one or more other features (e.g., the biasing member 112) of the medical device 100. The base member 110 may be formed from one or more materials including, for example, stainless steel (including medical grade stainless steel), nickel, titanium, platinum, gold, or one or more other materials. The base member 110 can be affixed to a distal portion of the biasing member 112. In embodiments, the base member 110 can be welded or otherwise permanently affixed to the base member 110.

The biasing member 112 can be a flexible structure capable of developing and/or imparting a spring force along a longitudinal dimension of the biasing member 112. The biasing member 112 can be formed from, for example, a metal such as stainless steel (including medical grade stainless steel), platinum, gold, titanium, or another suitably rigid material. The biasing member 112 may have a helical shape with one or more wires that surround the longitudinal axis 126 of the medical device 100. The biasing member 112 can have a length of between 1-20 mm, between 3-15 mm, between 5-10 mm, for example, approximately 7 mm. The biasing member 112 can have an outer diameter of between 1-5 mm, 2-4 mm, 2-3 mm, for example, approximately 2.5 mm. In some embodiments, the biasing member 112 may be a helical spring, and the helical spring can have a spring constant of between 0.01-0.02 N/mm, between 0.0115-0.0125 N/mm, between 0.0118-0.0120 N/mm, for example, approximately 0.0119 N/mm. In some embodiments, the helical spring may have between 10-40 coils, between 15-35 coils, between 29-31 coils, for example, approximately 30. In some embodiments, the biasing member 112 may extend between 15-30 mm during a medical procedure using the medical device 100. In some aspects, the biasing member 112 may extend between 20-25 mm during a medical procedure. The biasing member 112 may extend for a total distance of between 30-34 mm.

The needle 114 can be a needle structure that tapers from a proximal end 114*b* (nearer the proximal portion 102) to a distal end 114*a* (nearer the distal portion 106). The proximal end of the needle 114 may be fixedly coupled to the biasing member 112. In some embodiments, the needle 114 may be welded, soldered, or otherwise permanently affixed to the biasing member 112.

FIGS. 2A-2C show the medical device 100 in various configurations, for example, to help increase tension and/or traction. For example, the aspects of the medical device 100 shown in FIGS. 2A-2C may help to increase tension and/or traction applied to a tumor or lesion 10 surrounded by surrounding tissue 16 in an anatomy of a subject. The medical device 100 is shown in a body lumen 12 in a gastrointestinal (GI) tract of the subject, but the medical device 100 could be used in other portions of a subject's anatomy. The medical device 100 is removably coupled with the clip 118, which is in turn coupled to a wall 14 of the GI tract. The medical device 100 is coupled to the clip 118, for example, by positioning a portion of the connection member 108 within the clip 118 when coupling the clip 118 to the wall 14 of the GI tract. The connection member 108 can be of various sizes or shapes to accommodate the geometry of a subject's anatomy. With the needle 114 inserted into the lesion 10 and the connection member 108 removably coupled to the subject's anatomy at the wall 14, the biasing member 112 is placed under tension. That is, the biasing member 112 tends to cause the lesion 10 to pull away from the surrounding tissue 16, which may help to makeresection of the lesion 10 from the surrounding tissue 16 easier. \

FIG. 2B shows the lesion 10 having been partially resected from the surrounding tissue 16. The tension of the biasing member (e.g., due to the medical device 100 being coupled to the wall 14 and the lesion 10) helps to urge the lesion 10 away from the surrounding tissue 16. In this aspect, as the lesion 10 is resected, the biasing member 112 helps to lift at least a portion of the lesion 10 away from the surrounding tissue 16. Tension of the biasing member 112 continues to pull the portions of tissue still connected between the surrounding tissue 16 and the lesion 10, continuing to aid resection by increasing tension in those areas and preventing the resected portions of the lesion 10 from interfering with further resection. The tension put on the lesion 10 during clipping to the subject's anatomy may cause the biasing member 112 to expand in proportion to apply tension to the anatomy. Various aspects of the medical device 100 can be tuned and/or sized for specific anatomies or based on specific needs of the procedure. For example, a length of the connection member 108, a biasing force of the biasing member 112 (e.g., a spring tension or k-force of a spring, etc.), a size of the clip 118, or other factors or aspects of the implements used in the procedure.

FIG. 2C shows the lesion 10 fully resected from the surrounding tissue 16. The tension on the biasing member 112 is eased, and a user can remove the lesion 10. For example, a user may uncouple the clip 118 from the wall 14, may disconnect/cut the connection member 108 from the clip 118 using end effector 132, and/or remove the medical device 100 along with resected lesion 10. That is, the connection member 108 may be capable of being cut to sever the connection between the medical device 100 and the clip 118. The user may use, for example, an end effector 132 of a medical device system such as an endoscope 124 or other medical device system pulling the medical device 100 upward and away (e.g., proximally) from the surrounding tissue 16 to remove the lesion 10.

Figure 3A:
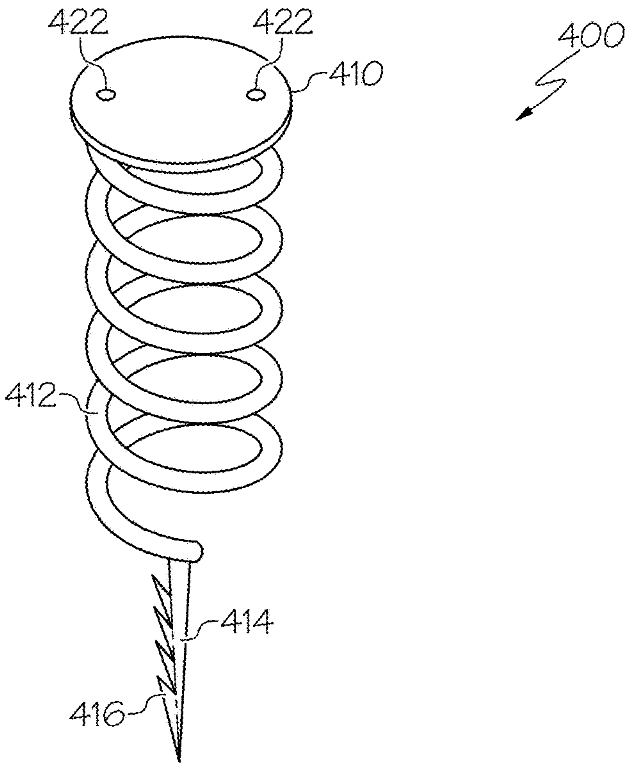
FIGS. 3A-3B illustrate additional details of different embodiments of a medical device, such as the medical device of FIG. 1.

FIG. 3A shows an embodiment of a medical device 400 including a base member 410 with one or more connection locations 422 for connecting a connection member (e.g., the connection member 108 of FIGS. 1 and 2A-2C) to the base member 410. As shown in FIG. 3A, the base member 410 may comprise a flat circular plate (i.e., a disc), and the disc may have two connection locations 422 (e.g., holes) for connecting the connection member to the disc. The medical device 400 also includes a biasing member 412 and a needle 414, with the needle 414 including one or more barbs 416. The needle 414 may be coupled directly to the biasing member 412 (e.g., via welding, soldering, one or more adhesives, etc.) The direct connection between the needle 414 and the biasing member 412 may help simplify manufacture of the medical device 400.

Figure 3B:
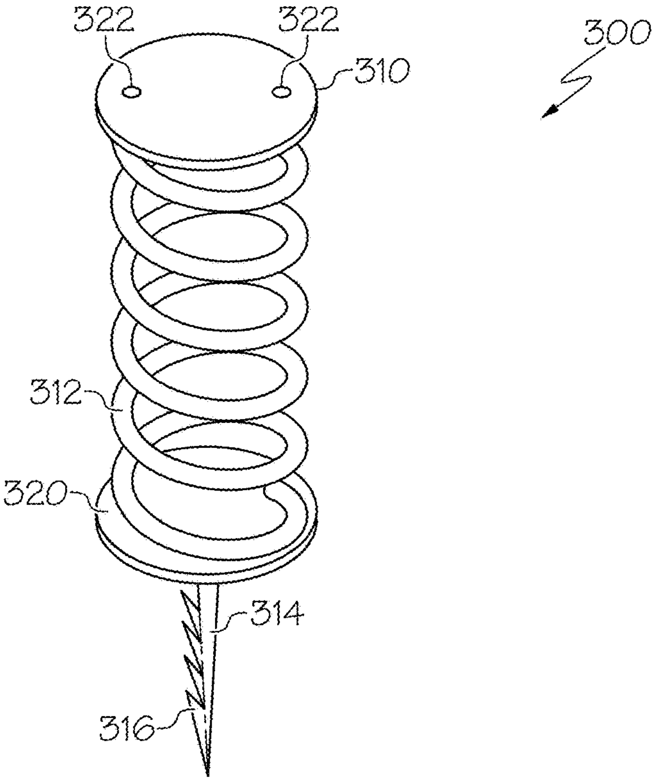

FIG. 3B shows an embodiment of a medical device 300 including a base member 310, a biasing member 312, a needle base member 320, and a needle 314. The needle 314 includes one or more barbs 316. The base member 310 can include connection locations 322 for connecting one or more connection members, such as the connection member 108 of FIGS. 1 and 2A-2C. The biasing member 312 may be coupled to the needle base member 320 using one or more connection methods, such as, for example, welding, soldering, etc. The needle base member 320 can help distribute the longitudinal forces acting on the needle 314 over a larger area, thus distributing the compression of the biasing member 312 over a larger area.

Figure 4A:
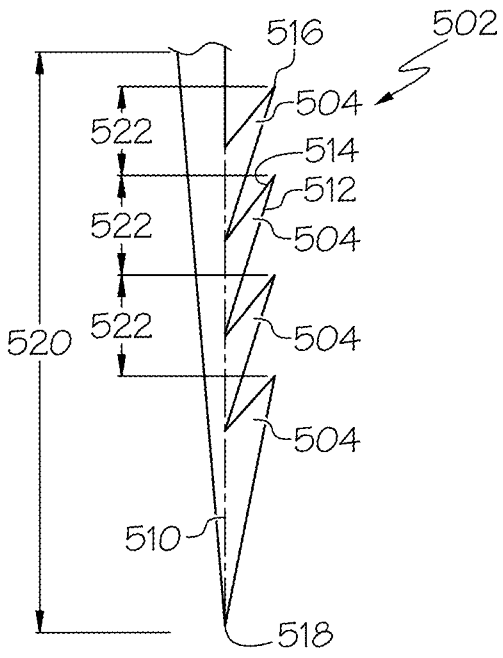
FIGS. 4A-4B illustrate additional details of different embodiments of a medical device, such as the medical device of FIG. 1.
Figure 4B:
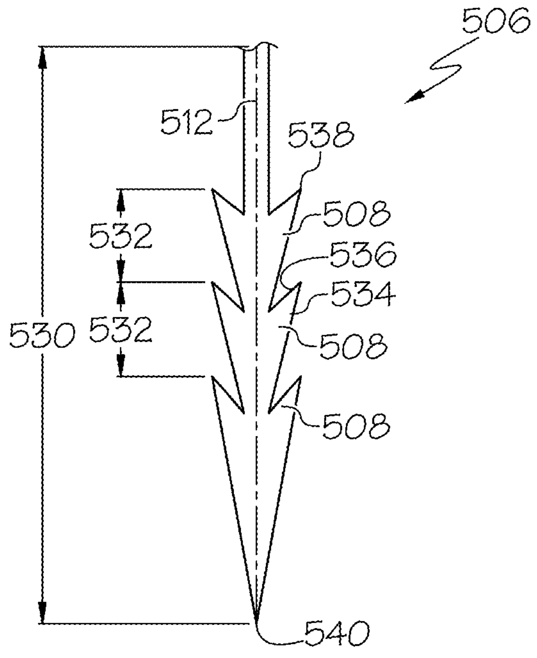

FIGS. 4A and 4B show different exemplary needles that may be incorporated in one or more portions of the medical device 100. Specifically, FIG. 4A shows a needle 502 including a plurality of barbs 504. FIG. 4B shows a needle 506 including a plurality of barbs 508. The barbs 504 can be on a single side of a central axis 510 of the needle 502. The barbs 508 can be on both sides of a central axis 510 of the needle 506 or may be barbs that form a generally conical shape conically encircling the central axis 510. As shown in FIG. 4A, the needle 502 can include four barbs. The barbs of the needles 502, 506 can be of any size and may each be of an equivalent size or the needles may be of different sizes. The barbs may incorporate a generally triangular profile with straight edges (as shown) or may incorporate one or more other profiles (e.g., curved profile, etc.)

Referring to FIG. 4A, each of the barbs 504 can include an outer face 512 and an inner face 514 that meet at a tip 516. The outer face 512 and the inner face 514 can have any geometry and form any relative angle between themselves and the longitudinal axis 510 of the needle 502. A tip 518 of the needle 502 can be a first distance 520 from the tip 516 of a first barb and the tips 516 of the barbs can be a second distance 522 from one another. In various embodiments, the first distance 520 and the second distance 522 can be different or equivalent.

Referring to FIG. 4B, each of the barbs 508 can include an outer face 534 and an inner face 536 that meet at a tip 538. The outer face 534 and the inner face 536 can have any geometry and form any relative angle between themselves and the longitudinal axis 510 of the needle 506. A tip 540 of the needle 506 can be a first distance 530 from the tip 538 of a first barb and the tips 538 of the barbs can be a second distance 532 from one another. In various embodiments, the first distance 530 and the second distance 532 can be different or equivalent.

Figure 5:
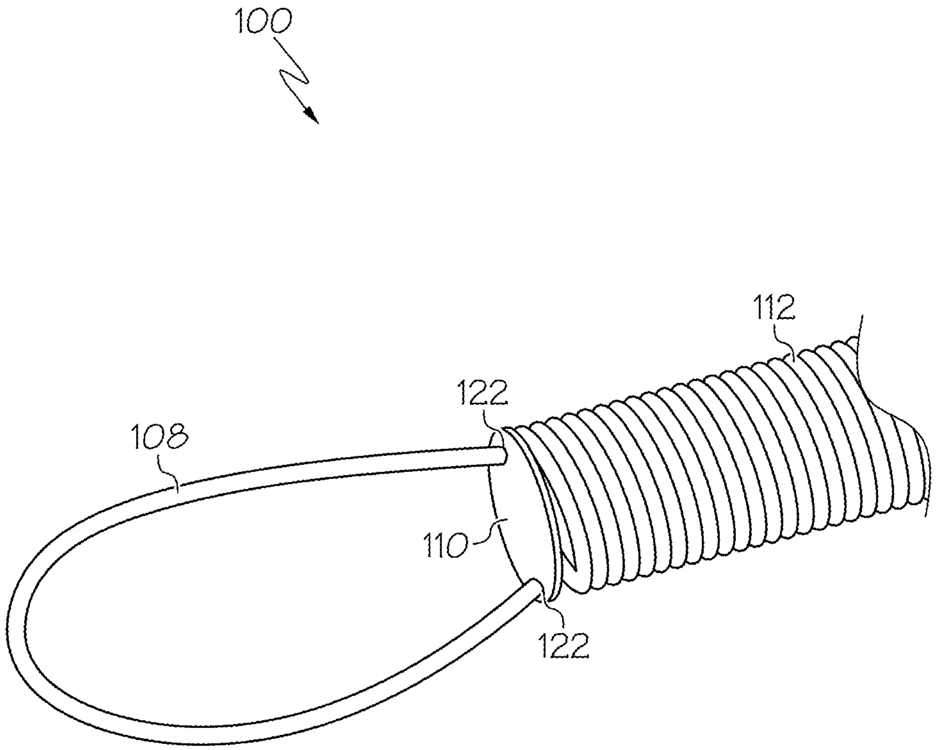
FIG. 5 illustrates additional details of a medical device, such as the medical device of FIG. 1.

FIG. 5 shows additional details of the medical device 100. The connection member 108 can be, for example, a flexible string, wire, filament, cable, thread, or other cuttable, frangible, breakable, or otherwise severable element that is connected to the biasing member 112 and capable of being placed under tension without breaking. The connection member 108 can be connected to the base member 110 by inserting opposite ends of the connection member 108 into connection portions 122 (e.g., holes) of the base member 110 and coupling ends of the connection member 108 (e.g., tying the ends together to form a loop, tying the ends separately for form respective knots, etc.). In these aspects, the ends of the connection member 108 may be too large to fit back through the connection portions 122. In some embodiments, the connection member 108 can be a semi-rigid or pliable material.

Figure 6:
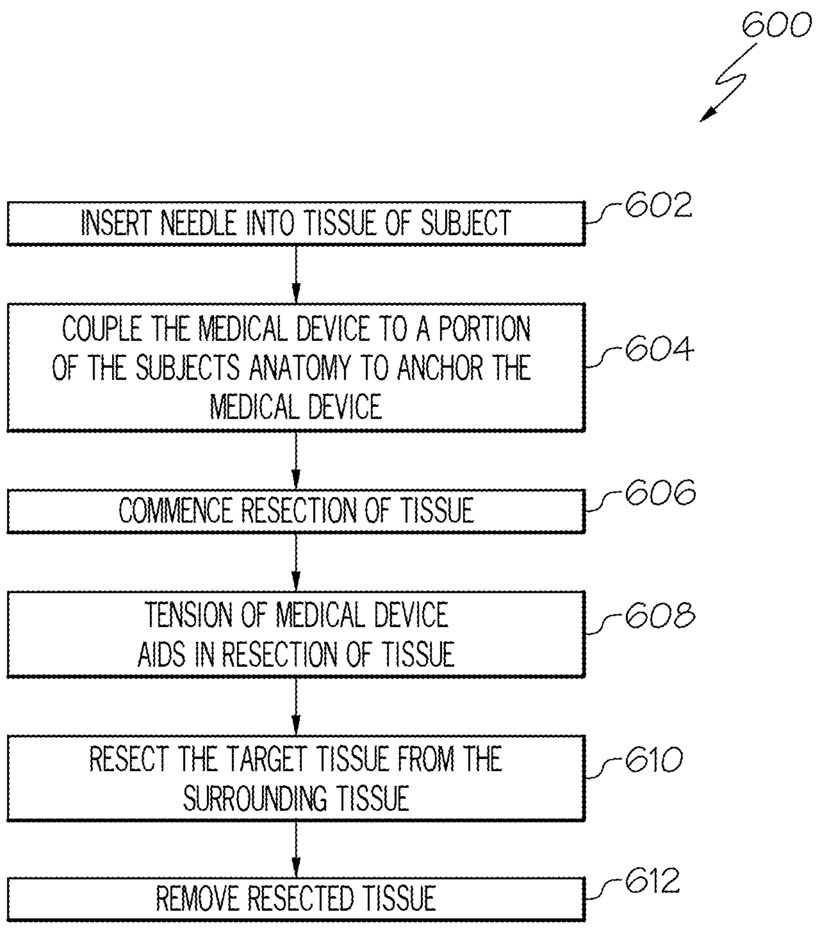
FIG. 6 is a flow diagram of an exemplary method of removing tissue using a medical device, such as the medical device of FIG. 1.

FIG. 6 shows a method 600 of removing a lesion or other tissue with a medical device. The method 600 is described with respect to the features shown in FIGS. 1 and 2A-20, but the method 600 is not limited by any of the specific features shown in these figures. For example, methods of using the medical device 100 can include additional or fewer steps and/or features to those shown and described herein.

At a step 602, a user (e.g., physician, medical technician, etc.) may insert the needle 114 into the tissue of a subject (e.g., a patient). As shown in FIGS. 2A-2C, the tissue is a lesion 10 in a GI tract of the subject, but other locations/types of tissue are contemplated. The user may insert the needle 114 to a sufficient depth such that at least one barb 116 is inserted into the tissue. The barb 116 may generally inhibit removal of the needle 114 from the tissue when the medical device 100 is pulled or urged away from the tissue, placing the medical device 100 and the tissue under tension. The subject tissue may have been partially cut from the surrounding tissue allowing the subject tissue to partially separate from the surrounding tissue as shown in FIG. 2A. In other embodiments, the subject tissue may not have yet been cut and the subject tissue may be put under tension with the surrounding tissue without any separation. This may enable incision/separation for the user as tissue under tension may more readily separate when cut. FIG. 2A does not show the devices or features (e.g., an electrosurgical knife) used to cut tissue, but shows tissue that has already been partially resected from the surrounding tissue.

At a step 604, a user may couple the medical device 100 to a portion of the subject's anatomy to anchor the medical device 100 and put the subject tissue (i.e., the lesion 10) under tension. In the embodiment shown in FIG. 2A, the medical device 100 is coupled to the subject's anatomy at the wall 14 of the GI tract via the connection member 108 with the clip 118 and the clip 118 grasps the wall 14 of the GI tract. The medical device 100 is connected to the clip 118 to pull the medical device 100 and hence the lesion 10. The lesion 10 pulls away from the surrounding tissue 16 putting the area of tissue between the lesion 10 and the surrounding tissue 16 under tension, which may help in a resection procedure.

The user may commence (or continue) tissue resection at the lesion 10 at a step 606. As the lesion 10 is resected, one or more portions of the lesion 10 may separate from the surrounding tissue 16. As one or more portions of the lesion 10 are separated from the surrounding tissue 16, portion(s) of the lesion 10 may move toward the wall 14, which eases the tension on the biasing member 112, for example, allowing the biasing member 112 to at least partially transition toward the relaxed or untensioned configuration of the biasing member 112.

Thus, at step 608, the medical device 100 may aid in the resection of tissue because as tension on the biasing member 112 continues to ease with increased cutting or resection of the lesion 10, the biasing member 112 will contract and help raise the tissue (e.g., the lesion 10) until the forces in the biasing member 112 and the tension forces in the tissue are equivalent. The biasing member 112 may help to prevent the portion of the lesion 10 that is pulled away from the surrounding tissue 16 from interfering with further resection still occurring at the interface between the lesion 10 and the surrounding tissue 16. The biasing member 112 may also help to keep the interface between the lesion 10 and the surrounding tissue 16 under tension, which may help to improve the precision of the resection at the interface.

At step 610, a user may fully resect the target tissue from the surrounding tissue and may remove the resected tissue. For example, step 610 may include fully separating the lesion 10 from the surrounding tissue 16. The fully resected tissue is thus free to move irrespective of the surrounding tissue 16 and the user can remove the tissue.

To remove the tissue, the user may decouple the medical device 100 from the wall 14 of the GI tract. For example, the user may cut the connection member 108, and/or may unclip the clip 118 from the wall 14. The lesion 10 may then be removed from the GI tract at step 612 using, for example, the end effector 132 of an endoscope 124 or other medical device system. Because the needle 114 is inserted into the lesion 10 with the one or more barbs 116, the tissue (e.g., the lesion 10) may remain attached to the needle 114 during the removal step.

Embodiments of this disclosure may be applicable to various and different medical procedures. In addition, certain aspects of the aforementioned embodiments may be selectively used in collaboration, or removed, during practice, without departing from the scope of the disclosure.

While principles of this disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

I claim:

1. A medical device comprising:

a connection member for connecting a homeostasis clip to the medical device;

a biasing member, wherein the biasing member biases the medical device toward a compressed configuration;

a needle with at least one barb, wherein the connection member comprises a loop made from one or more of nylon and linear low density polyethylene, wherein the connection member is connected to the biasing member such that, with the needle inserted into tissue past the at least one barb and the biasing member pulled toward a tensioned configuration by the homeostasis clip connected to the connection member, the needle and the at least one barb pull the tissue in a direction parallel to a direction of tension placed on the biasing member.

2. The medical device of claim 1, wherein the medical device includes a longitudinal axis and the biasing member applies tension along the longitudinal axis when pulled by the connection member.

3. The medical device of claim 1, further comprising a base member, wherein the base member is coupled to the connection member and the biasing member.

4. The medical device of claim 3, wherein the base member comprises a disc having two holes for connecting the connection member to the disc.

5. The medical device of claim 3, wherein the base member is a flat circular plate that includes one or more connection portions for connecting to the connection member.

6. The medical device of claim 5, further comprising a needle base member that couples the biasing member and the needle.

7. The medical device of claim 1, wherein the at least one barb of the needle comprises a plurality of barbs on at least two sides of the needle.

8. The medical device of claim 1, wherein the at least one barb comprises one or more projections that extend at an angle that is not parallel to a longitudinal axis of the needle.

9. The medical device of claim 1, wherein the connection member is configured to be removably coupled to a subject's anatomy with the homeostasis clip.

10. The medical device of claim 1, wherein the biasing member comprises stainless steel.

11. The medical device of claim 1, wherein the connection member is capable of being cut by an end effector of one or more medical device systems to sever the connection member.

* * * * *